(12) United States Patent
Lee et al.

(10) Patent No.: US 10,703,783 B2
(45) Date of Patent: Jul. 7, 2020

(54) CORYNEBACTERIUM SP. MICROORGANISMS HAVING L-LYSINE-PRODUCING ABILITY AND METHOD FOR PRODUCING L-LYSINE USING SAME

(71) Applicant: CJ Cheiljedang Corporation, Seoul (KR)

(72) Inventors: Seung Bin Lee, Gyeonggi-do (KR); Yoon Hee Chung, Seoul (KR); Hyung Joon Kim, Seoul (KR); Doo Jin Kang, Gyeonggi-do (KR); Seong Eun Bang, Gyeonggi-do (KR); Song Gi Ryu, Gyeonggi-do (KR)

(73) Assignee: CJ CHEILJEDANG CORPORATION (KR)

( * ) Notice: Subject to any disclaimer, the term of this patent is extended or adjusted under 35 U.S.C. 154(b) by 0 days.

(21) Appl. No.: 15/754,350

(22) PCT Filed: Jul. 27, 2016

(86) PCT No.: PCT/KR2016/008233
§ 371 (c)(1),
(2) Date: Feb. 22, 2018

(87) PCT Pub. No.: WO2017/034165
PCT Pub. Date: Mar. 2, 2017

(65) Prior Publication Data
US 2018/0251499 A1   Sep. 6, 2018

(30) Foreign Application Priority Data
Aug. 27, 2015  (KR) .................. 10-2015-0120739

(51) Int. Cl.
C12P 13/08 (2006.01)
C07K 14/34 (2006.01)
C12N 15/77 (2006.01)
C12R 1/15 (2006.01)

(52) U.S. Cl.
CPC ............. *C07K 14/34* (2013.01); *C12N 15/77* (2013.01); *C12P 13/08* (2013.01); *C12R 1/15* (2013.01)

(58) Field of Classification Search
None
See application file for complete search history.

(56) References Cited

U.S. PATENT DOCUMENTS 7,332,310 B2 * 2/2008 Nakagawa ............. C07K 14/34 435/115
2018/0251772 A1 * 9/2018 Song ...................... C12N 15/77

FOREIGN PATENT DOCUMENTS

| JP | 2002-191370 | 7/2002 |
|----|-------------|--------|
| JP | 2007-151551 | 6/2007 |
| JP | 2007-167064 | 7/2007 |
| KR | 10-0838035 B1 | 6/2008 |
| KR | 10-2013-0130377 A | 12/2013 |
| KR | 10-2015-0043717 A | 4/2015 |
| KR | 10-2015-0069340 A | 6/2015 |
| WO | WO 03/040681 A2 | 5/2003 |

OTHER PUBLICATIONS

Suzuki et al. (Applied and Environmental Microbiology, 2006, vol. 72, No. 5, pp. 3750-3755).*
International Search Report issued in PCT/KR2016/008233 dated Oct. 21, 2016.
NCBI, NCBI Reference Sequence No. WP_011013387.1 May 15, 2013.

* cited by examiner

*Primary Examiner* — Hope A Robinson
(74) *Attorney, Agent, or Firm* — Adsero IP

(57) ABSTRACT

The present invention relates to an L-lysine-producing microorganism of the genus *Corynebacterium* and a method for producing L-lysine using the same.

3 Claims, No Drawings
Specification includes a Sequence Listing.

CORYNEBACTERIUM SP. MICROORGANISMS HAVING L-LYSINE-PRODUCING ABILITY AND METHOD FOR PRODUCING L-LYSINE USING SAME

RELATED APPLICATIONS

This application is a National Stage Entry of International Application No. PCT/KR2016/008233, filed on Jul. 27, 2016, and claims the benefit of Korean Application No. 10-2015-0120739, filed on Aug. 27, 2015, each of which is hereby incorporated by reference in its entirety for all purposes as if fully set forth herein.

The instant application contains a Sequence Listing which has been filed electronically in ASCII format and is hereby incorporated by reference in its entirety. Said ASCII copy, created on Feb. 22, 2018, is named 0117_101_SL.txt and 4,328 bytes in size.

TECHNICAL FIELD

The present invention relates to an L-lysine-producing microorganism of the genus *Corynebacterium* and a method for producing L-lysine using the same.

BACKGROUND ART

L-lysine, a kind of essential amino acid, is used in the animal feed, human drug and cosmetic industries and is produced by fermentation using a microorganism of the genus *Corynebacterium* or the genus *Escherichia*.

A strain of the genus *Corynebacterium*, particularly *Corynebacterium glutamicum*, is a gram-positive microorganism which is extensively used to produce L-amino acid. For production of L-lysine, target-specific approaches have been mainly used, such as enhancement of the expression of genes encoding enzymes involved in L-lysine biosynthesis in a strain of genus *Corynebacterium*, or removal of genes unnecessary for L-lysine biosynthesis. In addition to these methods, a method of removing genes that are not involved in L-lysine biosynthesis, or a method of removing genes whose specific function is unknown, has also been used.

Accordingly, the present inventors have conducted extensive studies to identify effective characteristics capable of increasing lysine productivity. As a result, the present inventors have screened a microorganism producing a high concentration of L-lysine by randomly disrupting endogenous genes of a microorganism of the genus *Corynebacterium*, and have found that when a gene whose function has not yet been reported is disrupted in the screened microorganism, the L-lysine productivity of the microorganism increases, thereby completing the present invention.

PRIOR ART DOCUMENTS (Patent Document 1) KR 10-0838035 B1 (published on Jun. 12, 2008).

DISCLOSURE

Technical Problem

It is an object of the present invention to provide an L-lysine-producing microorganism of the genus *Corynebacterium*.

Another object of the present invention is to provide a method for producing L-lysine using the microorganism.

Technical Solution

To achieve the above objects, the present invention provides an L-lysine-producing microorganism of the genus *Corynebacterium* wherein a protein comprising an amino acid sequence of SEQ ID NO: 1 is inactivated.

The present invention also provides a method for producing L-lysine, comprising the steps of: culturing the microorganism of the present invention in a medium; and recovering L-lysine from the microorganism or the medium.

Advantageous Effects

The present invention provides a recombinant microorganism of the genus *Corynebacterium* having increased L-lysine productivity, which is obtained by inactivating a protein comprising an amino acid sequence of SEQ ID NO: 1, the function of which is unknown, in an L-lysine producing microorganism of the genus *Corynebacterium*. The recombinant microorganism of the genus *Corynebacterium* can produce L-lysine in high yield, and thus is industrially useful for the production of L-lysine.

MODE FOR INVENTION

Hereinafter, the present invention will be described in detail.

In a first aspect, the present invention provides an L-lysine-producing microorganism of the genus *Corynebacterium* wherein a protein comprising an amino acid sequence of SEQ ID NO: 1 is inactivated.

The protein comprising the amino acid sequence of SEQ ID NO: 1 is a protein endogenous in a microorganism of the genus *Corynebacterium*, or a hypothetical protein with unknown protein. A protein comprising an amino acid sequence having a homology of at least 80%, specifically at least 90%, more specifically at least 95%, particularly specifically at least 97%, to the amino acid sequence of SEQ ID NO: 1, may also be included in the scope of the protein comprising the amino acid sequence of SEQ ID NO: 1. In addition, it is obvious that a protein having an amino acid sequence comprising a deletion, modification, substitution or deletion of one or several amino acids is also included in the scope of the present invention, as long as it has a sequence having homology to the sequence of SEQ ID NO: 1 and has biological activity substantially equal or similar to that of the protein having the amino acid sequence of SEQ ID NO: 1.

Any nucleotide sequence capable of encoding the protein comprising the amino acid sequence of SEQ ID NO: 1 is included in the scope of the present invention. Specifically, the gene encoding the protein of SEQ ID NO: 1 may have a nucleotide sequence of SEQ ID NO: 2. In addition, a nucleotide sequence having a homology of at least 80%, specifically at least 90%, more specifically 95%, particularly specifically 97%, to the nucleotide sequence of SEQ ID NO: 2, may also be included in the scope of the present invention. In addition, variants of the sequence, which encode the same amino acid due to genetic code degeneracy, may also be included in the scope of the present invention.

As used herein, the term "homology" refers to identity to a given amino acid sequence or nucleotide sequence and may be expressed as percentage. In the specification, a homologous sequence having activity equal or similar to a given amino acid sequence or nucleotide sequence is expressed as "% homology".

The homology of the amino acid or nucleotide sequence can be determined by using, for example, algorithm BLAST (see Karlin and Altschul, Pro. Natl. Acad. Sci. USA, 90, 5873 (1993)) or FASTA by Pearson (see Methods Enzymol., 183, 63 (1990)). Programs called BLASTN and BLASTX have been developed on the basis of this algorithm BLAST.

As used herein, the term "inactivation" means that the expression of an endogenous gene is reduced compared to that in a parent strain, a strain before modification or a wild-type strain, or the gene is not expressed, or the gene has no activity or reduced activity even though it is expressed. In the present invention, inactivation may be achieved by any inactivation method known in the art. In the present invention, the inactivation method may be performed by at least one mutation selected from the group consisting of an insertion mutation obtained by inserting at least one base pair into the gene, a deletion mutation obtained by deleting at least one base pair from the gene, and a base pair transition or transversion mutation obtained by introducing a nonsense codon into the gene. Alternatively, the inactivation method may be performed by replacing the endogenous promoter of the gene with a weaker promoter or deleting all or part of the gene, but the scope of the present invention is not limited thereto.

The gene disruption method that is used in the present invention may be any gene disruption method known in the art and is not limited to a particular method. For example, light such as UV light or a chemical substance may be used to induce mutations, and a target gene-disrupted strain may be selected from the resulting mutants. In addition, the gene disruption method may be performed, for example, by introducing a nucleotide sequence or vector, which comprises a nucleotide sequence homologous to the target gene, into the microorganism, thereby inducing homologous recombination. In addition, the nucleotide sequence or vector introduced may comprise a dominant selection marker.

Examples of a vector that may be used to inactivate the target protein include natural or recombinant plasmids, cosmids, viruses, and bacteriophages. For example, the phage vector or cosmid vector that is used in the present invention may be pWE15, M13, λMBL3, λMBL4, λFIXII, λDASHII, λZAPII, λgt10, λgt11, Charon4A, Charon21A or the like, and the plasmid vector that is used in the present invention may be pDZ type, pBR type, pUC type, pBluescriptII type, pGEM type, pTZ type, pCL type, pET type or the like. A vector that may be used in the present invention is not particularly limited and may be an expression vector known in the art.

Introduction of the vector may be easily performed according to any conventional method known in the art. Generally, examples of this method include a $CaCl_2$ precipitation method, the Hanahan method with improved efficiency using dimethyl sulfoxide (DMSO) as a reducing agent in the $CaCl_2$ precipitation method, electroporation, a calcium phosphate precipitation method, a protoplast fusion method, an agitation method using silicon carbide fiber, a transformation method using PEG, dextran sulfate-, lipofectamine-, and dry/suppression-mediated transformations, etc.

As used herein, the term "trans format ion" means introducing a vector comprising a polynucleotide encoding a target protein into a host cell so as to enable the polynucleotide to be expressed or inactivated in the host cell. The polynucleotide may include DNA and RNA, which encode the target protein, or a promoter that reduces expression of the target protein, or a marker gene capable of inactivating expression of the target protein, etc. As long as the polynucleotide can be introduced in the host cell and expressed therein, it may be introduced in any form.

As a parent strain wherein the protein comprising the amino acid sequence of SEQ ID NO: 1 is to be inactivated, any microorganism having L-lysine productivity may be used without limitation. Examples of this microorganism include microorganisms belonging to the genus *Corynebacterium*, the genus *Brevibacterium*, the genus *Escherichia*, the genus *Enterbacter*, the genus *Erwinia*, the genus *Serratia* and the genus *Providencia*. Specifically, a microorganism of genus *Corynebacterium* may be used, and more specifically, a *Corynebacterium glutamicum* microorganism may be used.

As used herein, the expression "microorganism having L-lysine productivity" refers to a microorganism obtained by manipulating a generally known gene so as to be capable of producing L-lysine. For example, the microorganism may be a microorganism obtained by enhancing the expression of one or more genes selected from the group consisting of genes involved in L-lysine biosynthesis, including aspB (aspartate aminotransferase-encoding gene), lysC (aspartate kinase-encoding gene), asd (aspartate semialdehyde dehydrogenase-encoding gene), dapA (dihydrodipicolinate synthase-encoding gene), dapB (dihydrodipicolinate reductase-encoding gene) and lysA (diaminodipimelate decarboxylase-encoding gene), which are endogenous in a microorganism of the genus *Corynebacterium* and are involved in the production of L-amino acids. In addition, the microorganism may be a microorganism obtained by treating an L-leucine auxotrophic mutant strain with N-methyl-N'-nitro-N-nitrosoguanidine (NTG).

In a second aspect, the present invention provides a method for producing L-lysine, comprising the steps of: culturing the microorganism of the present invention in a medium; and recovering L-lysine from the microorganism or the medium.

The microorganism of the present invention is as described above.

In the method of the present invention, culturing of a microorganism of the genus *Corynebacterium* may be performed using any culture conditions and culture method known in the art.

For example, a medium that may be used for culture of a microorganism of the genus *Corynebacterium* is disclosed in Manual of Methods for General Bacteriology by the American Society for Bacteriology (Washington D.C., USA, 1981).

Sugar sources that may be used in the medium include sugars and carbohydrates such as glucose, saccharose, lactose, fructose, maltose, starch or cellulose; oils and fats such as soybean oil, sunflower oil, castor oil or coconut oil; fatty acids such as palmitic acid, stearic acid or linoleic acid; alcohols such as glycerol or ethanol; and organic acids such as acetic acid. These substances may be used individually or as a mixture, and the scope of the present invention is not limited thereto.

Nitrogen sources which may be used include compounds containing organic nitrogen, such as peptone, yeast extract, meat extract, malt extract, corn steep liquor, soybean meal and urea, or inorganic compounds such as ammonium sulfate, ammonium chloride, ammonium phosphate, ammonium carbonate and ammonium nitrate. The nitrogen sources may also be used individually or as a mixture, and the scope of the present invention is not limited thereto.

Phosphorus sources which may be used include potassium dihydrogen phosphate or dipotassium hydrogen phosphate or the corresponding sodium salts. The culture medium may also contain metal salts such as magnesium sulfate or iron sulfate, which are required for growth. Finally, essential growth substances such as amino acids and vitamins may be used in addition to the abovementioned substances. Moreover, suitable precursors may be added to the culture medium. Said substances may be added to the culture in a batch or a continuous manner by a suitable method during culturing.

The pH of the culture medium may be controlled by using basic compounds such as sodium hydroxide, potassium hydroxide, ammonia or aqueous ammonia or acidic compounds such as phosphoric acid or sulfuric acid in a suitable manner. Foaming can be controlled by using antifoaming agents such as fatty acid polyglycol esters. Aerobic conditions can be maintained by introducing oxygen or oxygen-containing gas mixtures (e.g., air) into the culture. The culture temperature is usually from 20° C. to 45° C., specifically from 25° C. to 40° C. Culturing may be continued until the amount of L-lysine produced reaches a desired level. Specifically, the culturing time is 10 to 160 hours.

In the method of the present invention, the culturing may be performed continuously or in a batch process or in a fed batch or repeated fed batch process. This culturing may be performed using any method well known in the art.

L-lysine can be isolated and analyzed by anion exchange chromatography with subsequent ninhydrin derivation. In addition, the method of the present invention comprises a step of recovering L-lysine. A method of recovering L-lysine from the microorganism or the culture medium is well known in the art. Examples of a method that may be used to recover 1-lysine include, but not limited to, filtration, anion exchange chromatography, crystallization and HPLC.

Hereinafter, the present disclosure will be described in further detail with reference to examples. It is to be understood, however, that these examples are for illustrative purposes only and are not intended to limit the scope of the present disclosure.

EXAMPLES

Example 1: Construction of Random Mutant Library Using Transposon

To obtain a strain having increased L-lysine productivity, a vector library was constructed in the following manner.

First, using *Corynebacterium glutamicum* KCCM11016P (this microorganism was disclosed as KFCC10881, and re-deposited with an International Depositary Authority under the Budapest Treaty under accession No. KCCM11016P; Korean Patent No. 10-0159812) as a parent strain, a plasmid obtained using the EZ-Tn5™ <R6Kγori/KAN-2>Tnp Transposome™ Kit (Epicentre) was transformed into the parent strain by an electric pulse method (Appl. Microbiol. Biotechnol. (1999) 52:541-545). Then, the strain was spread on a complex medium plate containing kanamycin (25 mg/l), thereby obtaining about 20,000 colonies.

Complex medium plate (pH 7.0):

10 g glucose, 10 g peptone, 5 g beef extract, 5 g yeast extract, 18.5 g brain heart infusion, 2.5 g NaCl, 2 g urea, 91 g sorbitol, and 20 g agar (per liter of distilled water).

Example 2: Random Mutant Library Screening Using Transposon

Each of about 20,000 colonies obtained in Example 1 was inoculated onto 300 μL of the following selective medium and cultured in a 96-deep-well plate at 32° C. and 1000 rpm for about 24 hours.

Selective medium (pH 8.0):

10 g glucose, 5.5 g ammonium sulfate, 1.2 g $MgSO_4 7H_2O$, 0.8 g $KH_2PO_4$, 16.4 g $K_2HPO_4$, 100 μg biotin, 1000 μg thiamine HCl, 2000 μg calcium-pantothenate, and 2000 μg nicotinamide (per liter of distilled water).

To analyze the amount of L-lysine produced in the culture, the ninhydrin method was used (Moore, S., Stein, W. H., Photometric ninhydrin method for use in the chromatography of amino acids. J. Biol. Chem. 1948, 176, 367-388).

After completion of the culturing, 10 μl of the culture supernatant was reacted with 190 μl of a ninhydrin reaction solution at 65° C. for 30 minutes, and then the absorbance at a wavelength of 570 nm was measured with a spectrophotometer. Based on the results of the measurement, about 60 colonies showing higher absorbance than the *Corynebacterium glutamicum* KCCM11016P strain used as the control were selected as mutant strains. Other colonies showed absorbance similar to or lower than that of the *Corynebacterium glutamicum* KCCM11016P strain used as the control.

About 60 strains selected as described above were cultured again in the same manner as described above, and then subjected to the ninhydrin reaction. As a result, the top ten mutant strains having increased L-lysine productivity compared to the *Corynebacterium glutamicum* KCCM11016P strain used as the parent strain were selected.

Example 3: Analysis of L-Lysine Productivity of Selected Random Mutant Strains In order to finally select strains whose L-lysine productivity was reproducibly increased from the ten mutants selected in Example 2, flask culture was performed using the following medium. After completion of the culturing, the concentration of L-lysine in the culture was analyzed by HPLC. The concentration of L-lysine produced by each of the mutant strains is shown in Table 1 below.

Seed medium (pH 7.0):

20 g glucose, 10 g peptone, 5 g yeast extract, 1.5 g urea, 4 g $KH_2PO_4$, 8 g $K_2HPO_4$, 0.5 g $MgSO_4.7H_2O$, 100 μg biotin, 1000 μg thiamine HCl, 2000 μg calcium-pantothenate, and 2000 μg nicotinamide (per liter of distilled water).

Production medium (pH 7.0):

100 g glucose, 40 g $(NH_4)_2SO_4$, 2.5 g soy protein, 5 g corn steep solids, 3 g urea, 1 g $KH_2PO_4$, 0.5 g $MgSO_4.7H_2O$, 100 μg biotin, 1000 μg thiamine chloride, 2000 μg calcium-pantothenate, 3000 μg nicotinamide, and 30 g $CaCO_3$ (per liter of distilled water).

TABLE 1

Concentrations of L-lysine produced by 10 selected random mutant strains

| Strains | | L-lysine (g/L) | | | |
|---|---|---|---|---|---|
| | | Batch 1 | Batch 2 | Batch 3 | Batch 4 |
| Control | KCCM1016P | 42.9 | 42.5 | 42.4 | 42.6 |
| 1 | KCCM11016P/mt-1 | 43.2 | 43.6 | 43.8 | 43.5 |

TABLE 1-continued

Concentrations of L-lysine produced by 10 selected random mutant strains

| | | L-lysine (g/L) | | | |
|---|---|---|---|---|---|
| | Strains | Batch 1 | Batch 2 | Batch 3 | Batch 4 |
| 2 | KCCM11016P/mt-2 | 43.0 | 43.1 | 43.4 | 43.2 |
| 3 | KCCM11016P/mt-3 | 42.6 | 42.8 | 42.9 | 42.8 |
| 4 | KCCM11016P/mt-4 | 43.1 | 42.8 | 42.9 | 42.9 |
| 5 | KCCM11016P/mt-5 | 43.0 | 42.9 | 42.7 | 42.9 |
| 6 | KCCM11016P/mt-6 | 41.0 | 41.7 | 41.6 | 41.4 |
| 7 | KCCM11016P/mt-7 | 43.2 | 42.8 | 42.7 | 42.9 |
| 8 | KCCM11016P/mt-8 | 53.2 | 53.1 | 53 | 53.1 |
| 9 | KCCM11016P/mt-9 | 42.7 | 42.5 | 42 | 42.4 |
| 10 | KCCM11016P/mt-10 | 48.9 | 48.2 | 48.5 | 48.5 |

Among the 10 selected mutant strains, KCCM11016P/mt-8 was finally selected as a strain whose L-lysine productivity was significantly increased.

Example 4: Identification of Causes of Increased L-Lysine Productivity of Finally Selected Strain In this Example, an experiment was performed on the mutant strain finally selected in Example 3 in order to identify genes disrupted by random insertion of the transposon.

Genomic DNA was extracted from KCCM11016P/mt-8, digested and then ligated, and the ligation product was transformed into 10 *E. coli* DH5α. The transformed *E. coli* cells were plated on an LB solid medium containing kanamycin (25 mg/L). Twenty transformed colonies were selected, and then plasmids containing an unknown gene portion were obtained. Sequencing was performed using primer 1 (SEQ ID NO: 3) and primer 2 (SEQ ID NO: 4) of the EZ-Tn5™ <R6Kγori/KAN-2>Tnp Transposom™ Kit. As a result, based on the nucleotide sequences registered in the NIH Genbank, it could be seen that the gene comprising the nucleotide sequence of SEQ ID NO: 2 was inactivated.

Primer 1 (SEQ ID NO: 3):
ACCTACAACAAAGCTCTCATCAACC;

Primer 2 (SEQ ID NO: 4):
CTACCCTGTGGAACACCTACATCT.

Example 5: Construction of Vector for Disruption of the Gene Comprising the Nucleotide Sequence of SEQ ID NO: 2

For construction of a recombinant vector capable of disrupting the gene comprising the nucleotide sequence of SEQ ID NO: 2 (identified in Example 4) in the chromosome of the strain of the genus *Corynebacterium*, primers 3 to 6 for constructing a fragment for disruption of the gene were synthesized and are shown in Table 2 below.

TABLE 2

Primers 3 to 6 for constructing fragment for disruption of gene

| Gene | Primers used | Nucleotide sequences |
|---|---|---|
| SEQ ID NO. | Primer 3 (SEQ ID NO: 5) | GAATTCTACACGCAGTGCCG AAACTTC |
| | Primer 4 (SEQ ID NO: 6) | TCGTATGTGCCTGGAATCAC GAGACAGC |
| | Primer 5 (SEQ ID NO: 7) | GATTCCAGGCACATACGACC AGGTCGCG |
| | Primer 6 (SEQ ID NO: 8) | GCAGGTCGACTCACCAACAC CATGACCACGCTT |

In order to delete the ORF region, primer 3 (SEQ ID NO: 5), primer 4 (SEQ ID NO: 6), primer 5 (SEQ ID NO: 7) and primer 6 (SEQ ID NO: 8) (Table 2) were synthesized based on SEQ ID NO: 2 so as to have an EcoRI restriction enzyme recognition site at the 5' end and a salI restriction enzyme recognition site at the 3' end. Using the synthesized primers, PCR [Sambrook et al, Molecular Cloning, a Laboratory Manual (1989), Cold Spring Harbor Laboratories] was performed using the chromosomal DNA of wild-type *Corynebacterium glutamicum* ATCC 13032 as a template. As a result, a DNA fragment comprising a 500-bp upstream region and a 500-bp downstream region, which correspond to the gene encoding the protein encoded by the nucleotide sequence of SEQ ID NO: 2, was obtained. The PCR was performed under the following conditions: 30 cycles, each consisting of denaturation at 95° C. for 30 sec, annealing at 50° C. for 30 sec, and polymerization at 72° C. for 1 min; followed by polymerization at 72° C. for 7 min. A pDZ vector (Korean Patent No. 10-0924065), which is not replicable in *Corynebacterium glutamicum*, and the fragment amplified by PCR, were treated with restriction enzymes EcorI and SalI for chromosomal introduction, and then ligated using DNA ligase. The ligation product was transformed into *E. coli* DH5a which was then plated on an LB solid medium containing kanamycin (25 mg/L).

A colony transformed with a plasmid having the desired gene inserted therein was selected by PCR, and then the plasmid was isolated using a plasmid extraction technique. The plasmid was named "pDZ-ΔMT8EH".

Example 6: Construction of Strain by Disruption of Gene Comprising Nucleotide Sequence of SEQ ID NO: 2 in *Corynebacterium glutamicum* KCCM11016P and Evaluation of L-Lysine Productivity of the Constructed Strain The recombinant plasmid pDZ-ΔMT8EH constructed in Example 5 was transformed into *Corynebacterium glutamicum* KCCM11016P, which is an L-lysine producing strain, by homologous recombination on the chromosome (van der Rest et al., Appl Microbiol Biotechnol 52:541-545, 1999).

Next, the transformed strain was subjected to second recombination on a solid plate medium containing 4% sucrose. After completion of the second recombination, disruption of the gene of SEQ ID NO: 2 on the chromosome of the transformed *Corynebacterium glutamicum* strain was confirmed by PCR using primer 3 and primer 6. The recombinant strain was named "*Corynebacterium glutamicum* KCCM11016P-MT8EH".

In order to analyze the L-lysine productivity of the constructed *Corynebacterium glutamicum* KCCM11016P-MT8EH strain, the constructed strain together with the parent strain *Corynebacterium glutamicum* KCCM11016P was cultured in the following manner.

Each of the parent strain *Corynebacterium glutamicum* KCCM11016P and the *Corynebacterium glutamicum* KCCM11016P-MT8EH strain constructed in Example 6 was inoculated into a 250-ml corner-baffled flask containing 25 ml of the following seed medium and was shake-cultured at 200 rpm at 30° C. for 20 hours. Next, 1 ml of each of the seed cultures was inoculated into a 250-ml corner-baffled flask containing 24 ml of the following production medium and was shake-cultured at 200 rpm at 30° C. for 72 hours. The composition of the seed medium and the composition of the production medium were as follows.

Seed medium (pH 7.0):
20 g glucose, 10 g peptone, 5 g yeast extract, 1.5 g urea, 4 g $KH_2PO_4$, 8 g $K_2HPO_4$, 0.5 g $MgSO_4 \cdot 7H_2O$, 100 μg biotin, 1000 μg thiamine HCl, 2000 μg calcium pantothenate, and 2000 μg nicotinamide (per liter of distilled water).

Production medium (pH 7.0):
100 g glucose, 40 g $(NH_4)_2SO_4$, 2.5 g soy protein, 5 g corn steep solids, 3 g urea, 1 g $KH_2PO_4$, 0.5 g $MgSO_4 \cdot 7H_2O$, 100 μg biotin, 1000μ thiamine HCl, 2000 μg calcium-pantothenate, 3000 μg nicotinamide, and 30 g $CaCO_3$ (per liter of distilled water).

After completion of the culturing, the amount of L-lysine produced was measured by HPLC (Waters 2478), and the concentration of L-lysine analyzed is shown in Table 3 below.

TABLE 3

Analysis of L-lysine productivity of KCCM11016P-MT8EH derived from KCCM11016P

| Strains | | L-lysine (g/L) | | | |
|---|---|---|---|---|---|
| | | Batch 1 | Batch 2 | Batch 3 | Average |
| Control group | KCCM11016P | 41.2 | 41.7 | 41.8 | 41.6 |
| Test Group | KCCM11016P-MT8EH | 54.9 | 55.2 | 54.5 | 54.9 |

From the results in Table 3 above, it was shown that when the gene comprising the nucleotide sequence of SEQ ID NO: 2 was disrupted in *Corynebacterium glutamicum* KCCM11016P which is an L-lysine producing strain, the L-lysine productivity of the recombinant strain increased by 32% on the average compared to that of the parent strain.

Thus, it was shown that the L-lysine productivity of the microorganism of the genus *Corynebacterium* could be increased by disrupting the gene comprising the nucleotide sequence of SEQ ID NO: 2 in the microorganism.

From the above-described results, it was seen that inactivating a hypothetical protein with unknown function by disrupting the gene comprising the nucleotide sequence of SEQ ID NO: 2 in the L-lysine producing strain was effective in increasing the L-lysine productivity of the strain. The strain KCCM11016P-MT8EH was named "CA01-2295" and was internationally deposited with the Korean Culture Center of Microorganisms (KCCM) on May 15, 2015 under accession number KCCM11697P.

Example 7: Construction of Strain by Disruption of Gene Comprising Nucleotide Sequence of SEQ ID NO: 2 in *Corynebacterium glutamicum* KCCM11347P and Evaluation of L-Lysine Productivity of the Constructed Strain In order to examine other L-lysine producing *Corynebacterium glutamicum* strains also have the same effect as described above, a strain wherein the gene comprising the nucleotide sequence of SEQ ID NO: 2 was disrupted was constructed from L-lysine-producing *Corynebacterium glutamicum* KCCM11347P (this microorganism was disclosed as KFCC10750, and re-deposited with an International Depositary Authority under the Budapest Treaty under accession No. KCCM11347P; Korean Patent No. 10-0073610) according to the same method as described in Example 6. The constructed strain was named "KCCM11347P-MT8EH".

The constructed strain was cultured in the same manner as described in Example 6. After completion of the culturing, the amount of L-lysine produced was measured by HPLC (Waters 2478), and the concentration of L-lysine analyzed is shown in Table 4 below.

TABLE 4

Analysis of L-lysine productivity of KCCM11347P-MT8EH derived from KCCM11347P

| | Strain | L-lysine (g/L) | | | |
|---|---|---|---|---|---|
| | | Batch 1 | Batch 2 | Batch 3 | Batch 4 |
| Control group | KCCM11347P | 37.9 | 38.1 | 37.9 | 38.0 |
| Test group | KCCM11347P-MT8EH | 47.5 | 47.4 | 47.6 | 47.5 |

From the results in Table 4 above, it was shown that when the gene comprising the nucleotide sequence of SEQ ID NO: 2 was disrupted in *Corynebacterium glutamicum* KCCM11347P which is an L-lysine producing strain, the L-lysine productivity of the strain increased by 25% on the average.

Thus, similarly to the results of Example 6, it was shown that the L-lysine productivity of the microorganism of the genus *Corynebacterium* could be increased by disrupting the gene comprising the nucleotide sequence of SEQ ID NO: 2 in the microorganism.

Example 8: Construction of Strain by Disruption of Gene Comprising Nucleotide Sequence of SEQ ID NO: 2 in *Corynebacterium glutamicum* CJ3P and Evaluation of L-Lysine Productivity of the Constructed Strain In order to examine whether other L-lysine producing *Corynebacterium glutamicum* strains also have the same effect as described above, a strain wherein the gene comprising the nucleotide sequence of SEQ ID NO: 2 was disrupted was constructed from L-lysine producing *Corynebacterium glutamicum* CJ3P (Binder et al. Genome Biology 2012, 13:R40), obtained by introducing three mutations [pyc(P458S), hom(V59A) and lysC(T311I)] into a wild-type strain, according to the same method as described in Example 6. The constructed strain was named "CJ3P-MT8EH".

The constructed strain was cultured in the same manner as described in Example 6. After completion of the culturing, the amount of L-lysine produced was measured by HPLC (Waters 2478), and the concentration of L-lysine analyzed is shown in Table 5 below.

TABLE 5

L-lysine productivity of CJ3P-MT8EH derived from CJ3P

|  | Strain | L-lysine (g/L) | | | |
| --- | --- | --- | --- | --- | --- |
|  |  | Batch 1 | Batch 2 | Batch 3 | Batch 4 |
| Control group | CJ3P | 8.2 | 8.1 | 8.4 | 8.2 |
| Test group | CJ3P-MT8EH | 10.1 | 10.3 | 9.8 | 10.1 |

From the results in Table 5 above, it was shown that when the gene comprising the nucleotide sequence of SEQ ID NO: 2 was disrupted in *Corynebacterium glutamicum* CJ3P which is an L-lysine producing strain, the L-lysine productivity of the strain increased by 23% on the average.

Thus, similarly to the results of Examples 6 and 7, it was shown that the L-lysine productivity of the microorganism of the genus *Corynebacterium* could be increased by disrupting the gene comprising the nucleotide sequence of SEQ ID NO: 2 in the microorganism.

Accession Number

Name of Depositary Institution: Korean Culture Center of Microorganisms;

Accession Number: KCCM11697P;

Date of Deposit: May 15, 2015.

The invention claimed is:

1. An L-lysine-producing microorganism obtained from *Corynebacterium glutamicum*, wherein a protein comprising an amino acid sequence of SEQ ID NO: 1 is inactivated.

2. The L-lysine-producing microorganism of claim 1, wherein the protein is encoded by the gene having the nucleotide sequence of SEQ ID NO: 2.

3. A method for producing L-lysine, comprising the steps of:

culturing the microorganism of claim 1 in a medium; and recovering L-lysine from the microorganism or the medium.

* * * * *

SEQUENCE LISTING

<160> NUMBER OF SEQ ID NOS: 8

<210> SEQ ID NO 1
<211> LENGTH: 193
<212> TYPE: PRT
<213> ORGANISM: Corynebacterium glutamicum

<400> SEQUENCE: 1

```
Met Ala Ala Asp Val Ala Thr Ser Ala Pro Ala Arg Gly Phe Phe His
1               5                   10                  15

Pro Ser Gly Asn Ser Arg Asp Leu Val Val Cys Gly Gly Phe Ala Ala
            20                  25                  30

Thr Gly Ala Ala Ser Glu Ile Arg Arg Ala Asn Val Ala Leu Val Leu
        35                  40                  45

Gly Ala Gly Leu Asn Gln Phe Thr Met Ala Phe Gly Glu Ala Phe Gly
    50                  55                  60

Glu Leu Ala Glu Val Leu Gln Val Asp Leu Glu Thr Gln Thr Thr Asn
65                  70                  75                  80

Pro Arg Ile Asn His Phe Ile Ser Ala Asp Asn Thr Thr Val Val Ala
                85                  90                  95

Ala Val Leu Leu Lys Leu Arg Thr Gln Asn Phe His Ala Pro Arg Arg
            100                 105                 110

Leu Tyr Leu Asp Asp Asn Pro Leu Thr Cys Pro Gly Gly Asp Ala Leu
        115                 120                 125

Ala Ala Asp Gly Arg Leu Asp Pro His Ser Leu Met Arg Gln Leu Asn
    130                 135                 140

Gly Ile Leu Pro Ala Asn Lys Phe Val Ala Ser Asp Gly Gly His Phe
145                 150                 155                 160

Ile Gly Gly Ala Asn Thr Tyr Phe Asp Leu Glu Ser Arg Asp Ser Ile
                165                 170                 175

Val Leu Leu Gly Thr Ala Phe Asn Pro Ser Ala Ser Ala Ser Pro Pro
            180                 185                 190

Pro
```

<210> SEQ ID NO 2
<211> LENGTH: 582
<212> TYPE: DNA
<213> ORGANISM: Corynebacterium glutamicum

<400> SEQUENCE: 2

```
ttggcagctg atgtagccac cagcgcgccc gcccgaggat tcttccatcc ctcaggaaac      60
tctcgcgacc tggtcgtatg tggaggtttc gctgcgaccg gtgcagcttc agaaatacgc     120
```

-continued

```
cgagccaacg tggcgcttgt gctgggcgcc ggtttgaacc aattcaccat ggcattcggg    180
gaggctttcg gtgaactcgc ggaagtgctc caagtggatc ttgaaacaca gaccaccaac    240
ccgcgcatta accatttcat tagcgcagat aacacaactg ttgtagccgc agtgctttta    300
aagcttcgta cacaaaattt ccacgcaccg cgccggctat acctggacga taatcctctg    360
acatgccctg gcggcgacgc ccttgcagcc gacggccgac tcgatccaca cagcctcatg    420
cgccaactta acggtatttt gccagctaac aagttcgtcg cctccgatgg cggacacttc    480
atcggagggg ccaacaccta cttcgacctg gaatcacgag acagcatcgt gcttttggga    540
accgccttca atccatcggc ctcggcttcc ccaccgccgt ag                      582
```

```
<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      Primer 1

<400> SEQUENCE: 3
acctacaaca aagctctcat caacc                                          25

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer 2

<400> SEQUENCE: 4
ctaccctgtg gaacacctac atct                                           24

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: Synthetic
      Primer 3

<400> SEQUENCE: 5
gaattctaca cgcagtgccg aaacttc                                        27

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: Synthetic
      Primer 4

<400> SEQUENCE: 6
tcgtatgtgc ctggaatcac gagacagc                                       28

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence: Synthetic
      Primer 5

<400> SEQUENCE: 7
```

```
gattccaggc acatacgacc aggtcgcg                                        28

<210> SEQ ID NO 8
<211> LENGTH: 33
<212> TYPE: DNA
<213> ORGANISM: Artificial Sequence
<220> FEATURE:
<223> OTHER INFORMATION: Description of Artificial Sequence: Synthetic
      Primer 6

<400> SEQUENCE: 8
gcaggtcgac tcaccaacac catgaccacg ctt                                  33
```